(12) United States Patent
Coyle et al.

(10) Patent No.: US 7,310,136 B2
(45) Date of Patent: Dec. 18, 2007

(54) METHOD AND APPARATUS FOR MEASURING PRISM CHARACTERISTICS

(75) Inventors: Dennis Joseph Coyle, Clifton Park, NY (US); Micah Sakiestewa Sze, Albany, NY (US); Masako Yamada, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 195 days.

(21) Appl. No.: 11/286,061

(22) Filed: Nov. 23, 2005

(65) Prior Publication Data

US 2007/0115465 A1    May 24, 2007

(51) Int. Cl.
   *G01N 9/00*     (2006.01)
   *G01N 21/00*    (2006.01)
   *G01N 21/41*    (2006.01)

(52) U.S. Cl. .................. 356/127; 356/128; 356/239.2

(58) Field of Classification Search ........ 356/124–128, 356/132, 239.1–329.2
   See application file for complete search history.

(56) References Cited

U.S. PATENT DOCUMENTS

| | | | |
|---|---|---|---|
| 5,724,108 A * | 3/1998 | Shibata | ................ 349/62 |
| 6,357,888 B1 * | 3/2002 | Takata et al. | ................ 362/620 |
| 6,731,380 B2 | 5/2004 | Amara et al. | |
| 2006/0066845 A1 * | 3/2006 | Capaldo et al. | .......... 356/239.1 |
| 2007/0115464 A1 * | 5/2007 | Harding et al. | .......... 356/239.2 |
| 2007/0115482 A1 * | 5/2007 | Harding et al. | ............. 356/600 |

OTHER PUBLICATIONS

Hwi Kim, Yong Jun Lim, Yang, B., Kyongsik Choi, Byoungho Lee, Geometrical Analysis of Optical Transmission Characteristics of Prism Sheet Layers, Optical Engineering, Dec. 2005, vol. 44, No. 12.*
JP 2003211540 A. Publication Date Jul. 29, 2003, "Manufacturing Method For Prismatic Sheet" (Abstract Only).

* cited by examiner

*Primary Examiner*—Gregory Toatley, Jr.
*Assistant Examiner*—Bryan J Giglio
(74) *Attorney, Agent, or Firm*—Cantor Colburn LLP (57) ABSTRACT

Disclosed herein is a method comprising illuminating a microstructured prism, or linear array of prisms of a prism sheet with an incident beam. The method further comprises making measurements of the refracted image of the beam on a measuring device to measure the distance disposed on an opposing side of the prism sheet from the side that the light beam is incident upon. Measurement of two angles of the refracted images of the beam on the ruled scale, measured twice, illuminating the sample at different angles are used in an equation to simultaneously provide the apex angle, the skew angle and the refractive index of the prism sheet.

52 Claims, 6 Drawing Sheets

Prism surface   Grooves

Back surface

METHOD AND APPARATUS FOR MEASURING PRISM CHARACTERISTICS

BACKGROUND

Disclosed herein is a method and an apparatus for measuring prism characteristics in a single prism, prism film or prism sheet. More specifically, the method and the apparatus are used for measuring the prism apex angle (hereinafter the apex angle), the prism skew angle (hereinafter the skew angle) and the refractive index of the material used in the prism.

Brightness enhancing display films generally termed "prism film" or "prism sheets" are used in liquid crystalline display devices in order to concentrate the light on a liquid crystalline layer. While the prisms in prism films or prism sheets can have any apex angle depending on the details of the backlight configuration and the desired output, it is generally desirable to employ prisms on the brightness enhancing display films that have apex angles of about 90 degrees. It is further desirable for a bisector of the apex angle of the prisms to be normal to the back surface of the brightness enhancing display film. If the bisector of the apex angle is not normal to the back surface, there is a reduction in the angular concentration of light. The angle between the bisector of the apex angle and a normal to the back surface is termed the "skew angle". If the prism apexes are perfectly aligned relative to the sheet itself, the prism skew angle is zero.

Prism sheets are manufactured by pressing a malleable material against a prism-shaped mold. Possible manufacturing processes include melt calendaring, embossing, injection molding, compression molding, casting and curing of thermally cured resin onto a substrate, and casting and curing of UV cured resin onto a substrate For example, the mold can be an electroform which is a replica of a drum that has a negative image of a prism surface machined on its outer surface by using a turning machine such as a lathe. Many other micro-machining techniques can also be employed, including those that create a flat master, such as micro-milling, and fly-cutting. The negative image of the prism surfaces can be manufactured with a cutting tool made of hard material such as diamond. It can also be manufactured through other micro-texturing methods such as laser engraving and photolithography.

When micromachining a prism sheet using a cutting tool, a misalignment of the cutting tool during the machining can result in a defective master. The defective master produces a defective mold, which then stamps out a defective brightness enhancing display film. Defective brightness enhancing display films generally have prism apex angles or skew angles that vary from the desired values. Differences of minutes or even seconds in the apex angle or in the skew angle can affect performance.

There exist many techniques to measure the refractive index of thin films or bulk solids, but most utilize expensive analytical devices such an ellipsometer, refractometer, or a prism coupler. In addition to the considerable overhead required of these analytical devices, one limitation is that they can only measure optically flat surfaces. In particular, they cannot be used to measure the refractive indices of prism sheets that contain microstructured prisms.

There exist many analytical techniques available to characterize the geometry of microstructures, such as stylus profileometry, confocal microscopy, scanning electron microscopy (SEM) and atomic force microscopy (AFM). However, they are expensive and labor-intensive. They are also usually destructive and suffer from measurement artifacts related to sample handling. In the case of measurements involving contact between the prism sheet and a portion of the analytical tool (e.g., a probe), the size and shape of the probe can also add artifacts to the measurement. Such measurements also cannot fulfill the demand for highly accurate, quantitative values of the apex angle and the skew angle of the prism sheets. In microscopy, such angles are generally extrapolated by processing micrographs of cross-sections.

The quality of the calculated angles is limited by the quality of the image itself; for example, the image may be out of focus or lack sufficient resolution. It is also difficult to make a cross-section of a sample absolutely perpendicular to the prism direction, be it through microtoming, or through dragging a contact probe across the sample. The sample can become deformed by the blade or the probe, as well. Hence, such techniques cannot provide quantitative values of the apex angle or the skew angle with the degree of accuracy demanded of optical applications.

Given the demands placed on optical applications, the manufacture of optical grade microstructured films requires accurate and reproducible measurements of both material refractive index and film geometry (e.g., the apex angle and the skew angle). In the case of the prism sheets, a refractive index difference in the third decimal place may affect performance of the end product (e.g., liquid crystalline displays).

There therefore does not exist any methods that can simultaneously measure the refractive index, apex angle, and skew angle of a microstructured prism film or sheet. In order to minimize geometric defects in the prisms it is desirable to use a method that can determine whether there are geometric defects present in the prism while at the same time detecting the refractive index of the material of the prism.

SUMMARY

Disclosed herein is a method comprising illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface; and wherein a third surface of the microstructured prism contacts a surface of a sheet substrate of the prism sheet; and further wherein the third surface is inclined at an angle of 90 degrees to the incident light beam; measuring a first distance "$d_1$" between a first image and a perpendicular to the surface of the substrate sheet on a measuring device that is disposed on an opposite side of the prism sheet from a light source used for the illuminating; wherein the perpendicular to the surface of the substrate sheet is taken at a point where the bisector of the apex angle of the prism meets the surface of the substrate sheet in contact with the third surface of the prism; and wherein the first image is obtained by refraction of the light beam from the first surface; measuring a second distance "$d_2$" between a second image and a perpendicular to the surface of the substrate sheet on the measuring device; wherein the second image is obtained by refraction of the light beam from the second surface; substituting values for $d_1$ and $d_2$ in the equation (1) and (2) below:

$$\sin(\theta_1 - \sin^{-1}(n_1/n_2 \sin(\theta_1))) = n_1/n_2 \sin(\tan^{-1}(d_2/d_3)) \quad (1)$$

$$\sin(\Phi_1 - \sin^{-1}(n_1/n_2 \sin(\Phi_1))) = n_1/n_2 \sin(\tan^{-1}(d_1/d_3)) \quad (2)$$

wherein "$d_3$" is the distance between the prism sheet and the measuring device, $n_1$ is the refractive index of the media in which the measurement is made and $n_2$ is the refractive index of the prism sheet; and determining at least one value for either $\theta_1$, $\Phi_1$ or $n_2$.

Disclosed herein too is a method comprising illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface; and wherein a third surface of the microstructured prism contacts a surface of a sheet substrate of the prism sheet; measuring a first distance "$d_1$" between a first image and a perpendicular to the surface of the substrate sheet on a measuring device that is disposed on an opposite side of the prism sheet from a light source used for the illuminating; wherein the perpendicular to the surface of the substrate sheet is taken at a point where the bisector of the apex angle of the prism meets the surface of the substrate sheet in contact with the third surface of the prism; and wherein the first image is obtained by refraction of the light beam from the first surface; measuring a second distance "$d_2$" between a second image and a perpendicular to the surface of the substrate sheet on the measuring device; wherein the second image is obtained by refraction of the light beam from the second surface; rotating the prism sheet or the light source through an angle $\beta$; wherein the angle $\beta$ is the difference in angle between the position occupied by the prism sheet when it is perpendicular to the incident light beam and the position occupied by the prism sheet after rotation; measuring a third distance "$d'_1$" between a third image and a perpendicular to the surface of the substrate sheet on a measuring device; wherein the third image is obtained by refraction of the light beam from the first surface; measuring a fourth distance "$d'_2$" between a fourth image and a perpendicular to the surface of the substrate sheet on the measuring device; wherein the fourth image is obtained by refraction of the light beam from the second surface; and simultaneously determining $\theta_1$, $\Phi_1$ and $n_2$ of the microstructured prism from the equations (1), (2), (3) and (4)

$$\sin(\theta_1-\sin^{-1}(n_1/n_2 \sin(\theta_1)))=n_1/n_2 \sin(\tan^{-1}(d_2/d_3)) \quad (1)$$

$$\sin(\Phi_1-\sin^{-1}(n_1/n_2 \sin(\Phi_1)))=n_1/n_2 \sin(\tan^{-1}(d_1/d_3)) \quad (2)$$

$$\sin(\theta_1-\sin^{-1}(n_1/n_2 \sin(\theta_1+\beta)))=n_1/n_2 \sin(\tan^{-1}(d'_2/d_3)-\beta) \quad (3)$$

$$\sin(\Phi_1-\sin^{-1}(n_1/n_2 \sin(\Phi_1+\beta)))=n_1/n_2 \sin(\tan^{-1}(d'_1/d_3)-\beta) \quad (4)$$

wherein "$d_3$" is the distance between the prism sheet and the measuring device, $n_1$ is the refractive index of the media in which the measurement is made and $n_2$ is the refractive index of the prism sheet.

Disclosed herein too is a method comprising illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface; wherein a third surface of the microstructured prism contacts a surface of a sheet substrate of the prism sheet; and further wherein the third surfaced is inclined at an angle of (90+$\beta$) degrees to the incident light beam; measuring a first distance "$d_1$" between a first image and a perpendicular to the surface of the substrate sheet on a measuring device that is disposed on an opposite side of the prism sheet from a light source used for the illuminating; wherein the perpendicular to the surface of the substrate sheet is taken at a point where the bisector of the apex angle of the prism meets the surface of the substrate sheet in contact with the third surface of the prism; and wherein the first image is obtained by refraction of the light beam from the first surface; measuring a second distance "$d_2$" between a second image and a perpendicular to the surface of the substrate sheet on the measuring device; wherein the second image is obtained by refraction of the light beam from the second surface; substituting values for $d_1$ and $d_2$ in the equation (3) and (4) below:

$$\sin(\theta_1-\sin^{-1}(n_1/n_2 \sin(\theta_1+\beta)))=n_1/n_2 \sin(\tan^{-1}(d'_2/d_3)-\beta) \quad (3)$$

$$\sin(\Phi_1-\sin^{-1}(n_1/n_2 \sin(\Phi_1+\beta)))=n_1/n_2 \sin(\tan^{-1}(d'_1/d_3)-\beta) \quad (4)$$

wherein "$d_3$" is the distance between the prism sheet and the measuring device, $n_1$ is the refractive index of the media in which the measurement is made and $n_2$ is the refractive index of the prism sheet; and determining at least one value for the apex angle, the skew angle or the refractive index from the equations (3) and (4).

Disclosed herein too is a method comprising illuminating a first surface and a second surface of a microstructured prism on a prism sheet with an incident light beam; wherein the microstructured prisms are disposed upon a substrate sheet; and wherein a back surface of the sheet substrate is perpendicular to the incident light beam; measuring a first distance "$d_1$" between a first image and a perpendicular to the back surface of the substrate sheet on a measuring device that is disposed on an opposite side of the prism sheet from a light source used for the illuminating; measuring a second distance "$d_2$" between a second image and the perpendicular to the back surface of the substrate sheet on the measuring device; substituting values for $d_1$ and $d_2$ in the equation (1) and (2) below:

$$\sin(\theta_1-\sin^{-1}(n_1/n_2 \sin(\theta_1)))=n_1/n_2 \sin(\tan^{-1}(d_2/d_3)) \quad (1)$$

$$\sin(\Phi_1-\sin^{-1}(n_1/n_2 \sin(\Phi_1)))=n_1/n_2 \sin(\tan^{-1}(d_1/d_3)) \quad (2)$$

wherein "$d_3$" is the distance between the prism sheet and the measuring device, $n_1$ is the refractive index of the media in which the measurement is made and $n_2$ is the refractive index of the prism sheet; $\theta_1$ is the angle between a normal to the first surface and the incident light beam and $\Phi_1$ is the angle between a normal to the second surface and the incident light beam; and determining at least one value for either $\theta_1$, $\Phi_1$ or $n_2$.

Disclosed herein too is a method comprising illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface; wherein a back surface of the prism sheet is inclined at an angle of (90+$\beta$) degrees to the incident light beam; measuring a first distance "$d_1$" between a first image and a perpendicular to the surface of the substrate sheet on a measuring device that is disposed on an opposite side of the prism sheet from a light source used for the illuminating; measuring a second distance "$d_2$" between a second image and the perpendicular to the surface of the substrate sheet on the measuring device; substituting values for $d_1$ and $d_2$ in the equation (3) and (4) below:

$$\sin(\theta_1 - \sin^{-1}(n_1/n_2 \sin(\theta_1 + \beta))) = n_1/n_2 \sin(\tan^{-1}(d'_2/d_3) - \beta) \quad (3)$$

$$\sin(\Phi_1 - \sin^{-1}(n_1/n_2 \sin(\Phi_1 + \beta))) = n_1/n_2 \sin(\tan^{-1}(d'_1/d_3) - \beta) \quad (4)$$

wherein "$d_3$" is the distance between the prism sheet and the measuring device, $n_1$ is the refractive index of the media in which the measurement is made and $n_2$ is the refractive index of the prism sheet; and determining at least one value for the apex angle, the skew angle or the refractive index from the equations (3) and (4).

Disclosed herein too is a method comprising illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface; and wherein a back surface of the prism sheet is perpendicular to the incident light beam; measuring a first distance "$d_1$" between a first image and a perpendicular to the surface of the substrate sheet on a measuring device that is disposed on an opposite side of the prism sheet from a light source used for the illuminating; measuring a second distance "$d_2$" between a second image and a perpendicular to the surface of the substrate sheet on the measuring device; rotating the prism sheet or the light source through an angle $\beta$; wherein the angle $\beta$ is the difference in angle between the position occupied by the prism sheet when its back surface is perpendicular to the incident light beam and the position occupied by the prism sheet after rotation; measuring a third distance "$d'_1$" between a third image and a perpendicular to the surface of the substrate sheet on a measuring device; measuring a fourth distance "$d'_2$" between a fourth image and a perpendicular to the surface of the substrate sheet on the measuring device; and simultaneously determining $\theta_1$, $\Phi_1$ and $n_2$ of the microstructured prism from the equations (1), (2), (3) and (4)

$$\sin(\eta_1 - \sin^{-1}(n_1/n_2 \sin(\theta_1))) = n_1/n_2 \sin(\tan^{-1}(d_2/d_3)) \quad (1)$$

$$\sin(\Phi_1 - \sin^{-1}(n_1/n_2 \sin(\Phi_1))) = n_1/n_2 \sin(\tan^{-1}(d_1/d_3)) \quad (2)$$

$$\sin(\theta_1 - \sin^{-1}(n_1/n_2 \sin(\theta_1 + \beta))) = n_1/n_2 \sin(\tan^{-1}(d'_2/d_3) - \beta) \quad (3)$$

$$\sin(\Phi_1 - \sin^{-1}(n_1/n_2 \sin(\Phi_1 + \beta))) = n/n_2 \sin(\tan^{-1}(d'_1/d_3) - \beta) \quad (4)$$

wherein "$d_3$" is the distance between the prism sheet and the measuring device, $n_1$ is the refractive index of the media in which the measurement is made and $n_2$ is the refractive index of the prism sheet.

Disclosed herein too is a method comprising illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface; rotating the prism sheet or the light source through a series of angles $\beta_1$, $\beta_2$; $\beta_3$, $\beta_4$, ..., $\beta_{m-1}$, $\beta_m$, wherein each of the angles $\beta_1$, $\beta_2$; $\beta_3$, $\beta_4$, ..., $\beta_{m-1}$, $\beta_m$, is the difference in angle between a position occupied by the prism sheet and the position occupied by the prism sheet prior to rotation; where m represents the number of rotational angles that the prism sheet $\beta$ is rotated through; measuring distances $d'_1$ and $d'_2$ at a rotational angle $\beta_1$, $d''_1$ and $d''_2$ at a rotational angle $\beta_2$, $d'''_1$ and $d'''_2$ at a rotational angle $\beta_3$, $d''''_1$ and $d''''_2$ at a rotational angle $\beta_4$, $d^{(m-1)'}_1$ and $d^{(m-1)'}_2$ at a rotational angle $\beta_{m-1}$ and $d^{m'}_1$ and $d^{m'hd\ 2}$ at a rotational angle $\beta_m$; wherein the distances are measured between the image and a perpendicular to a back surface of the prism sheet on a measuring device that is disposed on an opposite side of the prism sheet from a light source used for the illuminating; substituting the distances in the equations (9) through (20) below:

at angle $\beta_1$, $$\sin(\theta_1 - \sin^{-1}(n_1/n_2 \sin(\theta_1 + \beta_1))) = n_1/n_2 \sin(\tan^{-1}(d'_2/d_3) - \beta_1) \quad (9)$$

$$\sin(\Phi_1 - \sin^{-1}(n_1/n_2 \sin(\Phi_1 + \beta_1))) = n_1/n_2 \sin(\tan^{-1}(d'_1/d_3) - \beta_1) \quad (10)$$

at angle $\beta_2$, $$\sin(\theta_1 - \sin^-(n_1/n_2 \sin(\theta_1 + \beta_2))) = n_1/n_2 \sin(\tan^{-1}(d''_2/d_3) - \beta) \quad (11)$$

$$\sin(\Phi_1 - \sin^{-1}(n_1/n_2 \sin(\Phi_1 + \beta))) = n_1/n_2 \sin(\tan^{-1}(d''_1/d_3) - \beta_2) \quad (12)$$

at angle $\beta_3$, $$\sin(\theta_1 - \sin^{-1}(n_1/n_2 \sin(\theta_1 + \beta_3))) = n_1/n_2 \sin(\tan^{-1}(d'''_2/d_3) - \beta_3) \quad (13)$$

$$\sin(\Phi_1 - \sin^{-1}(n_1/n_2 \sin(\Phi_1 + \beta_3))) = n_1/n_2 \sin(\tan^{-1}(d'''_1/d_3) - \beta_3) \quad (14)$$

at angle $\beta_4$, $$\sin(\theta_1 - \sin^{-1}(n_1/n_2 \sin(\theta_1 + \beta_4))) = n_1/n_2 \sin(\tan^{-1}(d''''_2/d_3) - \beta_4) \quad (15)$$

$$\sin(\Phi_1 - \sin^{-1}(n_1/n_2 \sin(\Phi_1 + \beta_4))) = n_1/n_2 \sin(\tan^{-1}(d''''_1/d_3) - \beta_4) \quad (16)$$

at angle $\beta_{m-1}$, $$\sin(\theta_1 - \sin^{-1}(n_1/n_2 \sin(\theta_1 + \beta_{m-1}))) = n_1/n_2 \sin(\tan^{-1}(d^{(m-1)'}_2/d_3) - \beta_{m-1}) \quad (17)$$

$$\sin(\Phi_1 - \sin^{-1}(n_1/n_2 \sin(\Phi_1 + \beta_{m-1}))) = n_1/n_2 \sin(\tan^{-1}(d^{(m-1)'}_1/d_3) - \beta_{m-1}) \quad (18)$$

and at angle $\beta_m$, $$\sin(\theta_1 - \sin^{-1}(n_1/n_2 \sin(\theta_1 + \beta_m))) = n_1/n_2 \sin(\tan^{-1}(d^{m'}_2/d_3) - \beta_m) \quad (19)$$

$$\sin(\Phi_1 - \sin^{-1}(n_1/n_2 \sin(\Phi_1 + \beta_m))) = n_1/n_2 \sin(\tan^{-1}(d^{m'}_1/d_3) - \beta_m) \quad (20)$$

wherein "$d_3$" is the distance between the prism sheet and the measuring device, $n_1$ is the refractive index of the media in which the measurement is made and $n_2$ is the refractive index of the prism sheet; determining "m-1" values for $\theta_1$ and $\Phi_1$ respectively and "2(m-1)" values of $n_2$; and determining an average value for $\theta_1$, $\Phi_1$ and $n_2$ from the "m-1" values of $\theta_1$ and $\Phi_1$ respectively and the "2(m-1)" values of $n_2$.

Disclosed herein too is method comprising illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface; rotating the prism sheet or the light source through m angles of $\beta$; where m is a positive integer; measuring distances $d^{m'}_1$ and $d^{m'}_2$ at a rotational angle $\beta_m$; where $\beta_m$ represents $m^{th}$ angle of $\beta$; wherein the distances $d^{m'}_1$ and $d^{m'}_2$ are measured between the image and a perpendicular to a back surface of the prism sheet on a measuring device that is disposed on an opposite side of the prism sheet from a light source used for the illuminating; and substituting distances $d'''_1$ and $d'''_2$ in the equations (19) and (20)

$$\sin(\theta_1-\sin^{-1}(n_1/n_2 \sin(\theta_1+\beta_m)))=n_1/n_2 \sin(\tan^{-1}(d'''_2/d_3)-\beta_m) \quad (19)$$

$$\sin(\Phi_1-\sin^{-1}(n_1/n_2 \sin(\Phi_1+\beta_m)))=n_1/n_2 \sin(\tan^{-1}(d'''_1/d_3)-\beta_m) \quad (20)$$

wherein "$d_3$" is the distance between the prism sheet and the measuring device, $n_1$ is the refractive index of the media in which the measurement is made and $n_2$ is the refractive index of the prism sheet; determining "m−1" values for $\theta_1$ and $\Phi_1$ respectively and "2(m−1)" values of $n_2$; and determining an average value for $\theta_1$, $\Phi_1$ and $n_2$ from the "m−1" values of $\theta_1$ and $\Phi_1$ respectively and the "2(m−1)" values of $n_2$.

Disclosed herein too is an apparatus that uses the aforementioned methods.

DETAILED DESCRIPTION OF FIGURES

DETAILED DESCRIPTION

In the following description, like reference characters designate like or corresponding parts throughout the several views shown in the figures. It is also understood that terms such as "top", "bottom", "outward", "inward", and the like are words of convenience and are not to be construed as limiting terms. It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity).

Disclosed herein is an apparatus and a method that can be used to determine the apex angle as well as the skew angle of a microstructured prism disposed on a prism sheet. The microstructured prism generally has dimensions in the micrometer range. The method can also simultaneously be used to detect the refractive index of the resin used in a prism sheet. In one exemplary embodiment, the method comprises disposing a sample having a patterned surface such as, for example, a microstructured prismatic surface in the path of a monochromatic, collimated, light beam and measuring the location of two first order light peaks on a measuring device located on an opposing side of the prism sheet from the light source. A set of equations is then used to determine the apex angle of the prism sheet, the skew angle of the prism sheet as well as the refractive index of the resin used in the prism sheet.

The method is advantageous in that it simultaneously provides the refractive index of a material that does not have an optically flat surface in addition to determining the apex angle as well as the skew angle in a prism disposed on a prism sheet. The method is also advantageous in that it does not use expensive optical components such as, for example, an ellipsometer, a stylus profileometer, interferometer, prism coupler, refractometer, or the like, to obtain the aforementioned values. The method is non-destructive and the values of refractive index, apex angle and the skew angle are obtained without much loss of time or expenditure.

Figure 1:
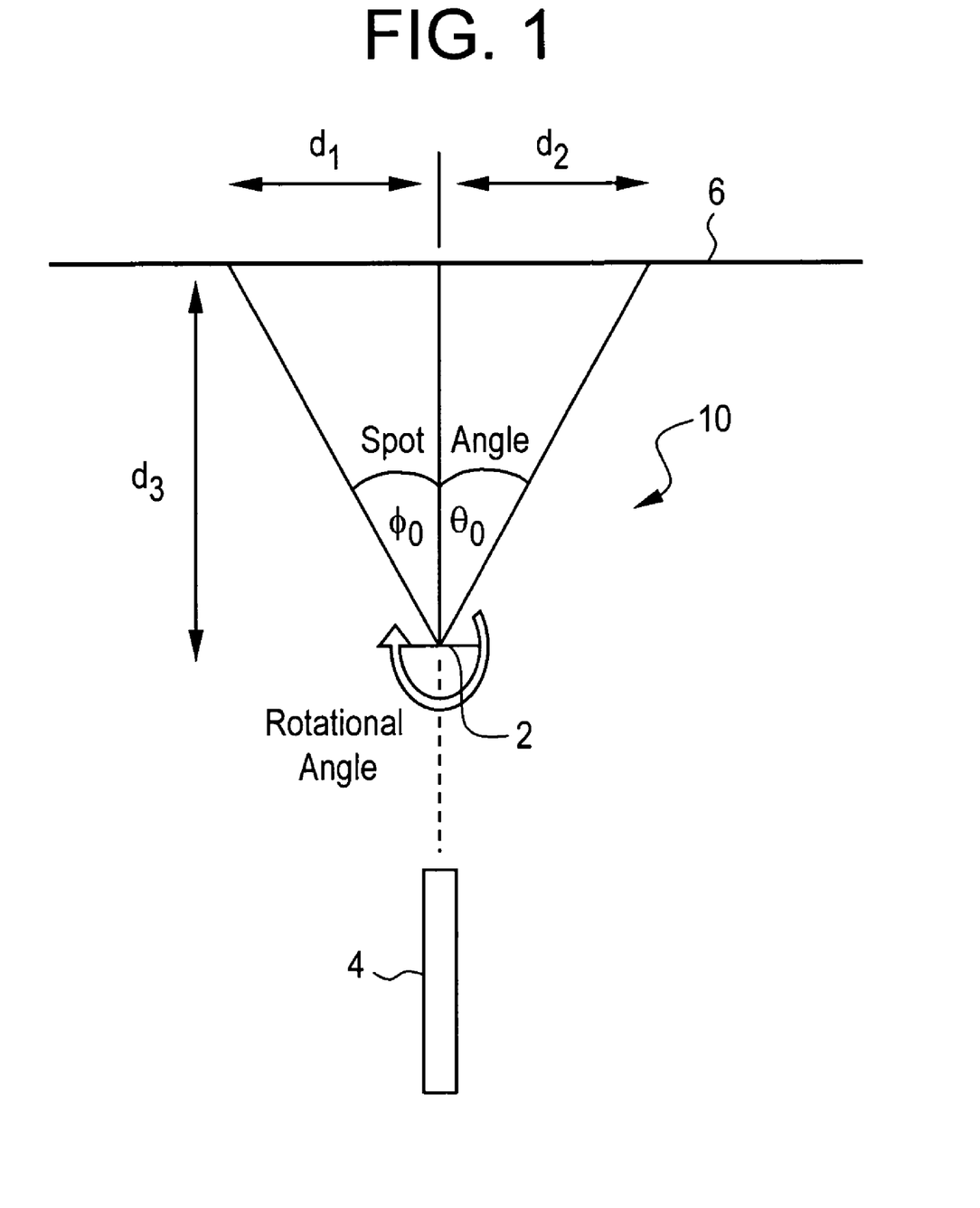
FIG. 1 is an exemplary depiction of a set-up 10 that is used for determining the apex angle, the skew angle and the refractive index $n_2$ of the prism sheet where convention is that $d_1$ is to the left of the light source (when the observer is facing the measuring device) and is assumed to be negative in value while $d_2$ is to the right of the light source and is assumed to be positive in value.

With reference now to the FIG. 1, which depicts an exemplary view of one embodiment of an apparatus 10 for simultaneously determining the apex angle, the alignment angle and the refractive index, the apparatus 10 comprises a light source 2 and a measuring device 6 between which is disposed the prism sheet 4. The light source 2 used to illuminate the prisms on the prism sheet comprises a monochromatic, narrow, collimated radiation source. In one embodiment, the light source 2 can be a laser. In another embodiment, the light source 2 is a 633 nanometer helium neon (HeNe) laser that operates at a power of 1 milliwatt (mW).

The sample-holder can be aligned by using a diffraction grating. The prism sheet 4 is mounted on an angular micrometer that is generally located at a distance of about 180 centimeters from the light source 2. The prism sheet 4 is mounted on the angular micrometer in a manner such that the microstructured prisms on the prism sheet 4 face the incident beam of light. The transmitted light from the prism sheet 4 is projected onto a measuring device 6. The measuring device is disposed on a side of the prism sheet 4 that is opposed to the side upon which the light beam is incident. The distance between the prism sheet 4 and the measuring device 6 indicated by $d_3$.

In one embodiment, two sets of measurements are made at two or more angles of inclination of the prism sheet 4 with respect to the incident beam. The measurements made for the first angle of inclination as shown in the FIG. 1 are $d_1$ and $d_2$. The measurements made at the second angle of inclination are $d'_1$ and $d'_2$. The distance $d_1$ or $d'_1$ is the distance between an image of the refracted beam from a first surface of a prism disposed upon the prism sheet, while the distance $d_2$ or $d'_2$ is the distance between an image of the refracted beam from a second surface of the same prism. Measuring $d_1$, $d'_1$, $d'_2$ and $d_2$ permit the apex angle, the skew angle and the refractive index $n_2$ of the prism sheet 4 to be simultaneously determined. Values for $d_1$, which lies to the left of the incident beam are assumed to be negative, while values for $d_2$, which lies to the right of the incident beam are assumed to be positive.

Figure 2:
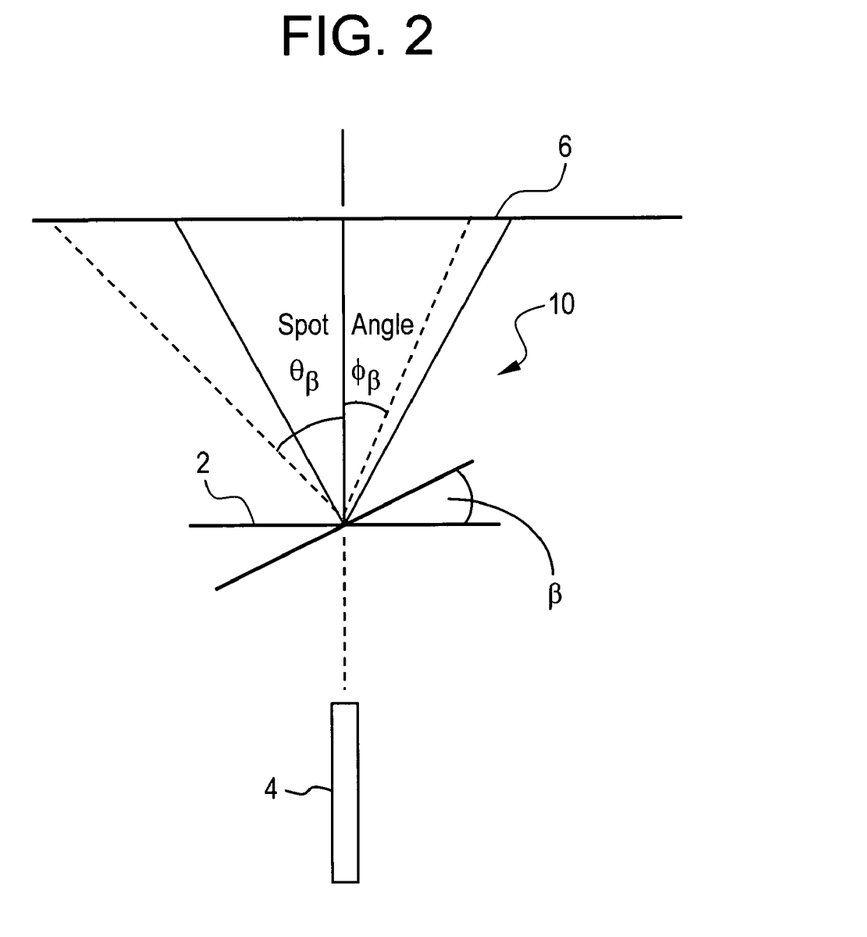
FIG. 2 is a depiction of the set-up 10 of FIG. 1, wherein the prism sheet 4 is rotated through an angle β where the assumed convention is that β is positive in the counter-clockwise direction.

In one embodiment, in one manner of proceeding, a first set of measurements are made with the prism sheet 4 perpendicular to the incident light beam. These measurements yield information about the refractive index "$n_2$" of the prism sheet. The refractive index of the media in which the measurement is made is designated as $n_1$. When the measurements are made in air, $n_1$ represents the refractive index of air. A second set of measurements are then made with the prism sheet 4 rotated at an angle with respect to the incident light beam. The angle β as shown in the FIG. 2 is the difference in angle between the position occupied by the prism sheet 4 when it is perpendicular to the incident light beam and the position occupied by the prism sheet 4 after rotation. The angle β is assumed to be positive in the counter-clockwise direction;

With reference now once again to the FIGS. 1 and 2, it may be seen in the FIG. 1, that since the angle β=0 degrees, the angle of refraction of the beam is denoted by $\Phi_0$ and $\theta_0$ respectively, while in the FIG. 2, the same angles are denoted by $\Phi_\beta$ and $\theta_\beta$ respectively to indicate that the prism sheet has been rotated through an angle β, where β≠0 degrees.

In one embodiment, the two measurements $d_1$ and $d_2$ or $d'_1$ and $d'_2$ made per prism sheet are made either by keeping the incident light source fixed and rotating the film sample. In another embodiment, the two measurements $d_1$ and $d_2$ or $d'_1$ and $d'_2$ made per prism sheet are made by keeping the film in a single position while rotating the light source. When either the film or the light source is rotated, slight changes in the position of the image of the refracted beam are noted and these changes are used to compute the apex angle, the skew angle and the refractive index of the prism sheet. As will be shown below, the apex angle, the skew angle and the refractive index of the prism sheet are all calculated by solving a set of non-linear equations.

The measuring device 6 is a ruled scale and is generally located at a distance $d_3$ effective to bring an image of the refracted beam into focus. In one embodiment, the distance between the measuring device 6 and the prism sheet 4 is about 50 to about 60 centimeters. In another embodiment, the distance between the measuring device 6 and the prism sheet 4 is about 52 to about 58 centimeters. In yet another embodiment, the distance between the measuring device 6 and the prism sheet 4 is about 54 to about 56 centimeters. In an exemplary embodiment, the distance between the measuring device 6 and the prism sheet 4 is about 54.60 to 55.5 centimeters.

In lieu of a ruled scale, any effective measuring device can be used to determine the location of the image of the refracted beam, as long as the location can be measured accurately. Examples include projecting the spots onto paper printed with calibrated lines or a grid and reading off the values; projecting the spots onto a surface treated with thermally or optically sensitive material to "burn" the locations of the spots to be measured later; projecting the spots onto an array of light detectors, for example a CCD, where the locations of the spots can be extracted electronically (either analog or digital signal); projecting the spots onto a wall and using a ruler, tape measure, or other scale to measure the location of the spots.

Figure 3:
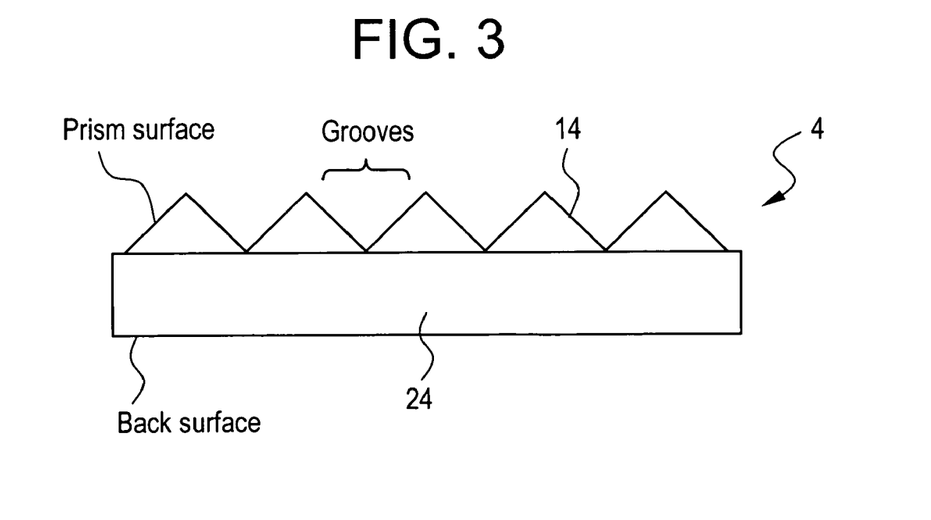
FIG. 3 is an exemplary embodiment of a prism sheet 4 that comprises microstructured prisms 14 disposed upon a sheet substrate 24.

FIG. 3 is an exemplary depiction of one embodiment of the prism sheet. As may be seen in the FIG. 3, the prism sheet 4 comprises acrylate microstructured prisms 14 disposed on a polyester or polycarbonate sheet substrate 24. The prism sheet can alternatively be entirely constructed of one material and thus have no internal interfaces. The valleys and the peaks of the prism sheet are also collectively referred to as prism grooves. The surface of the prism is referred to as the prism surface. The surface of the sheet opposed to the prism surface is termed the back surface.

The acrylate microstructured prisms 14 generally have a height "h" of about 12 to about 25 micrometers and a base width "w" of about 24 to about 50 micrometers. The prism sheet has a refractive index indicated by "$n_2$". While the FIG. 3 shows a single interface between the prisms 14 and the sheet substrate 24, there can be more than a single interface in the prism sheet 4. It is generally desirable that the interface is flat. For example, a multi-layered plastic substrate can also be used as a prism sheet so long as the layers are parallel to each other. Thus, the method described herein is equally applicable to a monolithic prism film (one without interfaces) as it is to a prism disposed upon a single or multilayered sheet substrate.

Figure 4:
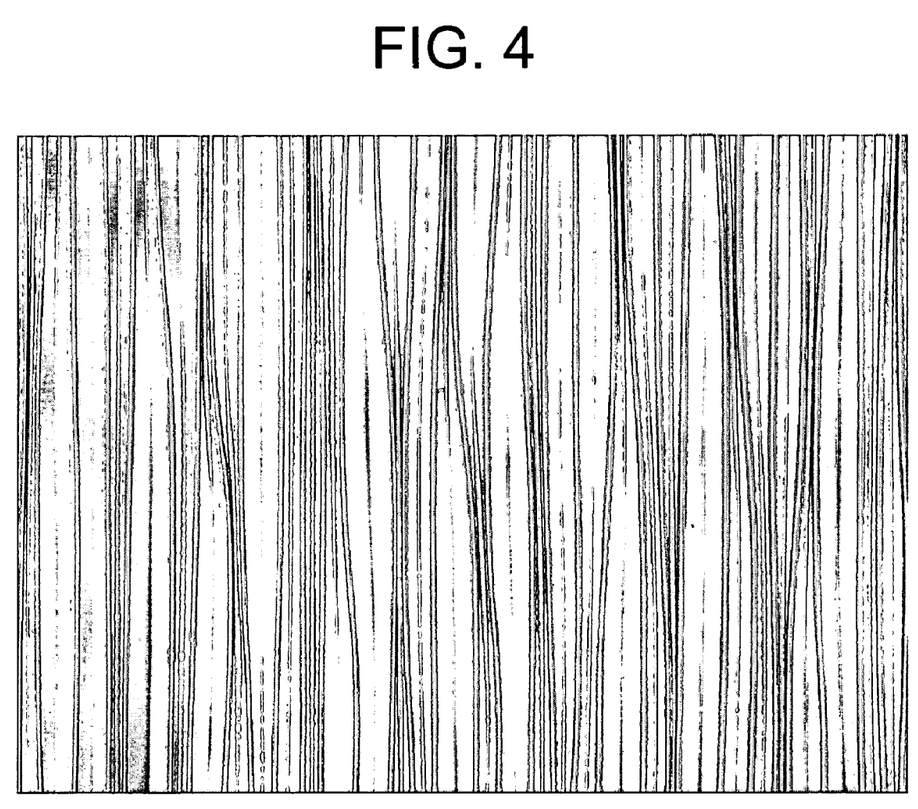
FIG. 4 is a photomicrograph showing microstructured prisms disposed upon a sheet substrate.

FIG. 4 shows a photomicrograph of the prisms that are disposed upon a prism sheet 4. As can be seen from the FIG. 4, the prisms are not evenly distributed on the surface of the prism sheet 4 and exhibit curvature (angular modulation). As noted above, measuring the apex angle and skew angle of a straight microstructured prism sheet (e.g., one where the prisms are evenly distributed and which do not exhibit any angular modulation) is difficult when using equipment such as, for example, a microtome, a contact profileometer, scanning and transmission electron microscopes, atomic force microscopes and other methods that explore a cross-section of the prism sheet.

This difficulty is compounded when the prism grooves are randomized, i.e., they exhibit angular modulation, as it is more difficult to move a blade or a probe from one of the aforementioned instruments in a direction that is perpendicular to the predominant direction of the prisms. It is also to be noted that the cross-section of any prism sheet will give a distribution of apex angles and skew angles. The disclosed method therefore enables the apex angle and skew angle to be measured for prism sheets with randomized, as well as straight grooves, as the spots projected on the ruled scale are averaged over several prisms due to the finite width of the incident light source. For randomized prism grooves, the projected spots are diffuse, with the center of the diffuse spot providing information about the apex angle and skew angle. For straight prism grooves, the projected spots are sharp, with the center of the sharp spot providing information about the apex angle and skew angle.

Figure 5:
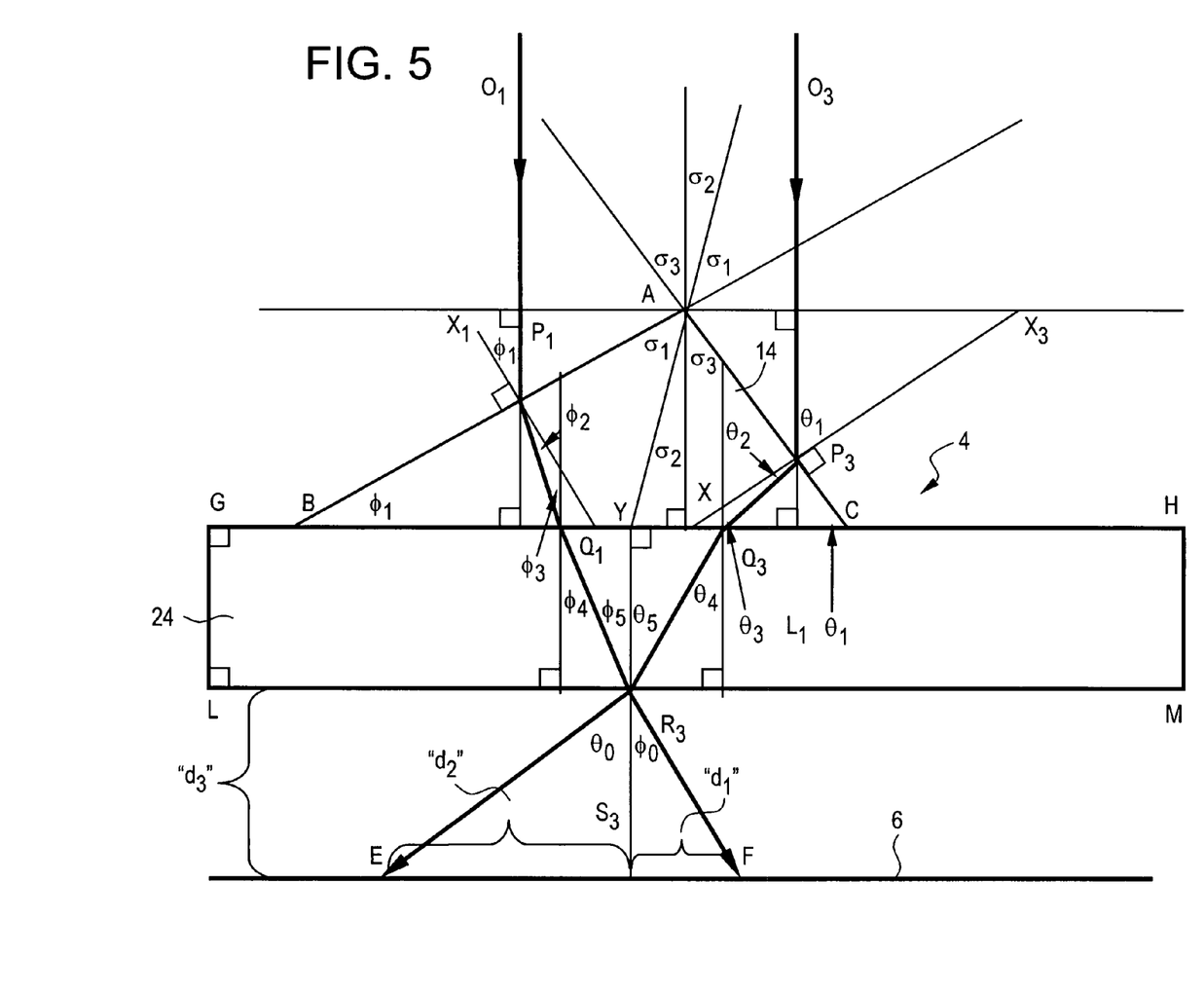
FIG. 5 is an exemplary depiction of one embodiment of a geometrical construction that provides equations that can be used to determine the skew angle and the refractive indices.

An exemplary solution to the problem of simultaneously determining the skew angle and the refractive index is arrived at with the geometrical construction depicted in the FIG. 5. The construction in the FIG. 5 represents one method of determining the refractive index, when the light from the light source is incident upon the prism sheet such that the beam is perpendicular to the surface of the prism sheet that is opposed to the surface upon which the beam is incident. It is also assumed that the back surface of the film (that is opposed to the surface upon which the microstructured prisms are disposed) is flat. The FIG. 5 depicts the beam of light as being incident on a single prism for purposes of simplicity. In reality, the illuminating beam is incident upon several prisms at the same time. The image formed on the ruled scale represents the projection of the image of the beam after being refracted through several prisms.

As can be seen from the FIG. 5, the prism ABC has a first surface AB and a second surface AC upon which the light beam is incident. "A" represents the apex of the prism 14, while the third surface "BC" is disposed upon the sheet substrate 24. The sheet substrate is depicted by GHML. The third surface of the prism BC is disposed upon the surface GH of the sheet substrate GHLM. The angle ABC (hereinafter angle B) of the prism is represented by $\Phi_1$ while the angle ACB (hereinafter angle C) is represented by $\theta_1$. Since the prism depicted in the FIG. 5 is skewed (i.e., it is not an equilateral triangle), the bisector of the angle A is not the same as the normal to the surface BC. In the FIG. 5, line AY represents the bisector of the angle A while AZ represents the normal to the surface BC. The angle $\sigma_2$ as shown in the FIG. 5 therefore represents the skew angle.

From the FIG. 5 the sum of $\Sigma\sigma_i$ represents the apex angle A of the prism. $\sigma_1$ is defined such that $\sigma_1=\sigma_2+\sigma_3$. In other words, the line separating $\sigma_1$ from the other two angles ($\sigma_2$ and $\sigma_3$) bisects the prism apex angle. Ideally, as $\sigma_2$ approaches zero, $\sigma_1$, and $\sigma_3$ become equal.

In determining the apex angle, the skew angle and the refractive index, a convention is adopted such that $d_1$ that is to the left of the light source (when an observer is facing the image) is negative, while $d_2$, which is to the right of the light source is positive. In general, if all angles that are counterclockwise to the normal to a particular surface are assumed to be positive angles, then the apex angle A is equivalent to $180-(\theta_1-\Phi_1)$ degrees, where $\theta_1$ is positive and $\Phi_1$ is negative. Under this convention, the skew angle $\sigma_2$ is equivalent to $(\theta_1+\Phi_1)/2$. Other coordinate conventions may also be adopted as long as all positive and negative signs are consistently applied throughout.

A ray of light $O_1P_1$ incident upon the first surface AB of the prism at point $P_1$ at an angle $\Phi_1$ with respect to a normal $P_1X_1$ to the face AB, is refracted by the prism and takes the path $P_1Q_1$, whereupon it undergoes refraction at $Q_1$ and travels along the path $Q_1R_3$ prior to exiting the prism sheet 4 and impinging on the measuring device 6 at point F. The ray $P_1Q_1$ makes an angle $\Phi_2$ with respect to the normal to the first surface AB of the prism 4 and an angle $\Phi_3$ with respect to the normal to the surface GH of the sheet substrate GHML. The ray $Q_1R_3$ makes an angle $\Phi_4$ with respect to the normal to the surface GH of the sheet substrate and an angle $\Phi_5$ with respect to the normal to the surface LM of the sheet substrate prior to exiting the sheet substrate and impinging on the measuring device and forming a first image at point F. The ray $R_3F$ makes an angle $\Phi_0$ with respect to the normal to the surface of the sheet substrate LM.

Similarly, a ray of light $O_3P_3$ incident on the second surface AC of the prism is refracted and travels along the path $P_3Q_3$ and $Q_3R_3$ prior to exiting the prism sheet 4 and impinging on the measuring device 6 at point E. The ray $O_3P_3$ is incident upon the second surface AC at an angle $\theta_1$ with respect to a normal $P_3X_3$ at the face AC, while the ray $P_3Q_3$ makes an angle $\theta_2$ with respect to the normal $P_3X_3$ to AC and an angle $\theta_3$ with respect to the normal at GH. The ray $Q_3R_3$ makes and angle $\theta_4$ with respect to the normal at GH and an angle $\theta_5$ with respect to the normal at LM. The ray $R_3E$ makes an angle $\theta_0$ with the normal at LM prior to impinging on the measuring device and forming a second image at point E. From FIG. 5, it may also be seen that the distance between the sheet substrate and the measuring device (e.g., $R_3S_3$) is termed the "adjacent" distance and is denoted as "$d_3$" in the equations that follow. The distance of the image of the beam from the "imaginary" image of the apex on the measuring device is termed the "opposite" distance. For example, in the FIG. 5, the opposite distance between the second image E and $S_3$ (the imaginary image of the apex) is called the second distance and is denoted as "$d_2$", while the distance between the first image F and $S_3$ is called the first distance and is denoted as "$d_1$".

From the construction depicted in the FIG. 5, the following equations (1) and (2) may be arrived at.

$$\sin(\theta_1-\sin^{-1}(n_1/n_2 \sin(\theta_1)))=n_1/n_2 \sin(\tan^{-1}(d_2/d_3)) \quad (1)$$

and $$\sin(\Phi_1-\sin^{-1}(n_1/n_2 \sin(\Phi_1)))=n_1/n_2 \sin(\tan^{-1}(d_1/d_3)) \quad (2)$$

From the equations (1) and (2), if the prism is aligned perfectly and the apex angle is assumed to be 90 degrees, i.e., $\theta_1=\Phi_1=45$ and the refractive index $n_2$ of the prism sheet can be arrived at. As noted above, $n_1$ is the refractive index of the ambient media that the measurements are made in.

In attempting to solve equations (1) and (2), it is to be noted that there 2 equations with 3 unknown terms (i.e., $\theta_1$, $\Phi_1$ and $n_2$). In order to determine the apex angle and the skew angle, it is desirable for one of the terms from amongst $\theta_1$, $\Phi_1$ and $n_2$ to be known or to be arrived at independently. In one embodiment, $n_2$, the refractive index of the prisms can be obtained independently from a supplier or from a refractive index table, thereby permitting a solution of equations (1) and (2) and obtaining values for $\theta_1$ and $\Phi_1$. In another embodiment, if none of the values of $\theta_1$, $\Phi_1$ or $n_2$ are known beforehand, a solution to equations (1) and (2) can be obtained via iteration, thereby obtaining values for $\theta_1$, $\Phi_1$ and $n_2$. If a solution is obtained via iteration, then it is possible that two values of $n_2$ can be obtained. These values are generally proximate to each other and may differ only by an amount that can be attributed to experimental error.

Figure 6:
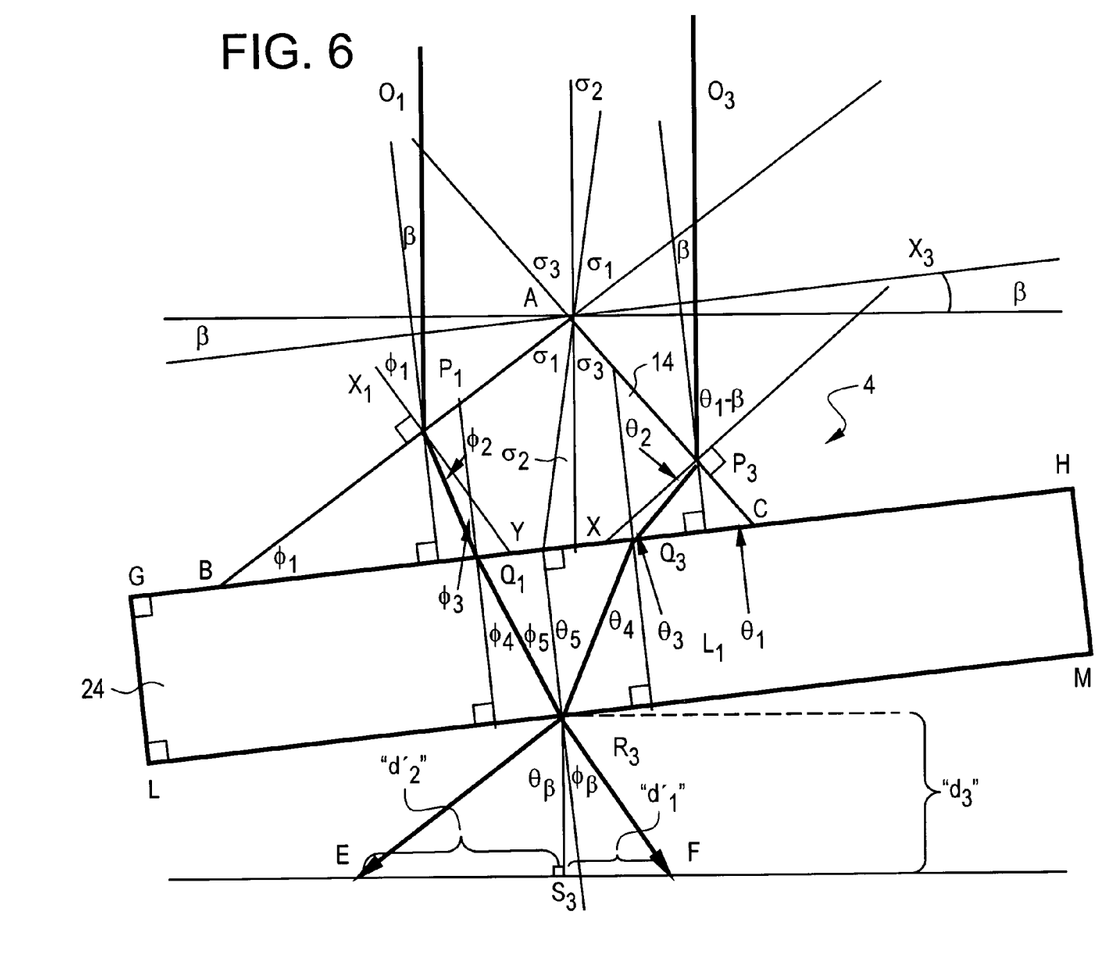
FIG. 6 is an exemplary depiction of another embodiment of a geometrical construction that provides equations that can be used to determine the skew angle and the refractive indices; in this construction either the light source or the prism sheet is rotated at an angle β from the position occupied in the FIG. 5.

As noted above, either the film or the light source can be rotated through two different angles and measurements made to determine the apex angle, the skew angle and the refractive index. FIG. 6 depicts the embodiment, when the prism sheet 4 or the light source is rotated through an angle $\beta$. As noted above, the angle $\beta$ is the difference in angle between the position occupied by the prism sheet 4 when it is perpendicular to the incident light beam and the position occupied by the prism sheet 4 after rotation. The value of $\beta$ can be measured and is therefore known. The construction in the FIG. 6 is similar to that in FIG. 5, except that all angles have to be compensated for by the angle $\beta$. Thus the back surface is inclined at an angle equal to $(90+\beta)$ degrees to the incident beam. The distance between E and $S_3$ (the imaginary image of the apex) is termed a third distance and is denoted by "$d'_1$", while the distance between F and $S_3$ is termed a fourth distance and is denoted by "$d'_2$". The construction in FIG. 6 leads to two more equations (3) and (4), which can be used to solve for the apex angle, the skew angle and the refractive index. Equations (3) and (4) are as follows:

$$\sin(\theta_1-\sin^{-1}(n_1/n_2 \sin(\theta_1+\beta)))=n_1/n_2 \sin(\tan^{-1}(d'_2/d_3)-\beta) \quad (3)$$

$$\sin(\Phi_1-\sin^{-1}(n_1/n_2 \sin(\Phi_1+\beta)))=n_1/n_2 \sin(\tan^{-1}(d'_1/d_3)-\beta) \quad (4)$$

By solving the equations (1), (2) (3) and (4) above, information about the apex angle, the skew angle and the refractive index can be simultaneously obtained. The conventions, described above, for the signs of $d_1$ and $d_2$ are followed here as well.

In one embodiment, information about the apex angle, the skew angle and the refractive index can be simultaneously obtained by solving equations (1) and (3). Information about the apex angle, the skew angle and the refractive index can also be simultaneously obtained by solving equations (2) and (4). In solving the equations (1) and (3) along with equations (2) and (4), two values of $n_2$ may be arrived at.

These values generally lie within the limits of experimental error and can be averaged to obtain a single value if desired.

In one embodiment, the methods seen in the FIG. 5 and the FIG. 6 can be combined to obtain a better approximation of the apex angle, the skew angle as well as the refractive index of the prism sheet.

In yet another embodiment, the first and second measurements may be made with the prism sheet rotated at angles $\beta_1$ and $\beta_2$ with respect to the prism sheet. As noted above, the angles $\beta_1$ and $\beta_2$ represent the difference in angles between the position occupied by the prism sheet 4 when it is perpendicular to the incident light beam and the successive positions occupied by the prism sheet 4 after rotation. In this case the refractive index, the apex prism and the skew angle can be determined by solving the equations (5), (6), (7) and (8) below.

$$\sin(\theta_1 - \sin^{-1}(n_1/n_2 \sin(\theta_1+\beta))) = n_1/n_2 \sin(\tan^{-1}(d''_2/d_3) - \beta_1) \quad (5)$$

$$\sin(\Phi_1 - \sin^{-1}(n_1/n_2 \sin((\Phi_1+\beta)))) = n_1/n_2 \sin(\tan^{-1}(d''_1/d_3) - \beta_1) \quad (6)$$

$$\sin(\theta_1 - \sin^{-1}(n_1/n_2 \sin(\theta_1+\beta))) = n_1/n_2 \sin(\tan^{-1}(d'''_2/d_3) - \beta_2) \quad (7)$$

$$\sin(\Phi_1 - \sin^{-1}(n_1/n_2 \sin(\Phi_1+\beta_2))) = n_1/n_2 \sin(\tan^{-1}(d'''_1/d_3) - \beta_2) \quad (8)$$

where the terms $\theta_1$, $\Phi_1$, and $d_3$ have their usual meanings as indicated above and wherein $d''_1$ and $d''_2$, are the respective distances between the refracted images of the beam and a normal to the surface of the sheet substrate (represented by $S_3$ in the FIG. 5 when the sheet substrate is normal to the incident beam), when the prism sheet is rotated through $\beta_1$, while $d'''_1$ and $d'''_2$ are the distances between the images the normal to the sheet substrate, when the prism sheet is rotated through $\beta_2$.

As can be seen above, when 2 different angles of $\beta$ are used for making measurements, there are 4 equations with 3 unknown quantities $\theta_1$, $\Phi_1$ and $n_2$. Thus by solving equations (5) and (7) along with (6) and (8), the values of $\theta_1$, $\Phi_1$, and $n_2$ can be obtained. As explained above, two values of $n_2$ are obtained and these can be averaged to obtain a more precise value for the refractive index of the prisms.

In a similar manner, by taking measurements at 3 different angles of $\beta$ ($\beta_1$, $\beta_2$, and $\beta_3$), 6 equations are obtained having 3 unknown quantities $\theta_1$, $\Phi_1$ and $n_2$. By solving these 6 equations, we can get 2 estimates for each angle $\theta_1$, $\Phi_1$ along with 4 estimates of $n_2$. In a similar manner, by taking measurements at "m" different angles of $\beta$ ($\beta_1$, $\beta_2$, $\beta_3$, $\beta_4$, ... $\beta_m$) it is possible to get "m-1" values of each angle $\theta_1$ and $\Phi_1$ along with "2(m-1)" values of $n_2$. It is to be noted that m is an integer that can have values of greater than or equal to about 5, greater than or equal to about 10, greater than or equal to about 100, if desired.

The equations resulting from performing m measurements are shown below as follows:

At angle $\beta_1$, $$\sin(\theta_1 - \sin^{-1}(n_1/n_2 \sin(\theta_1+\beta_1))) = n_1/n_2 \sin(\tan^{-1}(d'_2/d_3) - \beta_1) \quad (9)$$

$$\sin(\Phi_1 - \sin^{-1}(n_1/n_2 \sin(\Phi_1+\beta_1))) = n_1/n_2 \sin(\tan^{-1}(d'_1/d_3) - \beta_1) \quad (10)$$

at angle $\beta_2$, $$\sin(\theta_1 - \sin^{-1}(n_1/n_2 \sin(\theta_1+\beta_2))) = n_1/n_2 \sin(\tan^{-1}(d''_2/d_3) - \beta_2) \quad (11)$$

$$\sin(\Phi_1 - \sin^{-1}(n_1/n_2 \sin(\Phi_1+\beta_2))) = n_1/n_2 \sin(\tan^{-1}(d''_1/d_3) - \beta_2) \quad (12)$$

at angle $\beta_3$, $$\sin(\theta_1 - \sin^{-1}(n_1/n_2 \sin(\theta_1+\beta_3))) = n_1/n_2 \sin(\tan^{-1}(d'''_2/d_3) - \beta_3) \quad (13)$$

$$\sin(\Phi_1 - \sin^{-1}(n_1/n_2 \sin((\Phi_1+\beta_3)))) = n_1/n_2 \sin(\tan^{-1}(d'''_1/d_3) - \beta_3) \quad (14)$$

at angle $\beta_4$, $$\sin(\theta_1 - \sin^{-1}(n_1/n_2 \sin(\theta_1+\beta_4))) = n_1/n_2 \sin(\tan^{-1}(d''''_2/d_3) - \beta_4) \quad (15)$$

$$\sin(\Phi_1 - \sin^{-1}(n_1/n_2 \sin(\Phi_1+\beta_4))) = n_1/n_2 \sin(\tan^{-1}(d''''_1/d_3) - \beta_4) \quad (16)$$

and so on.

At angle $\beta_{m-1}$, $$\sin(\theta_1 - \sin^{-1}(n_1/n_2 \sin(\theta_1+\beta_{m-1}))) = n_1/n_2 \sin(\tan^{-1}(d^{(m-1)'}_2/d_3) - \beta_{m-1}) \quad (17)$$

$$\sin(\Phi_1 - \sin^{-1}(n_1/n_2 \sin(\Phi_1+\beta_{m-1}))) = n_1/n_2 \sin(\tan^{-1}(d^{(m-1)'}_1/d_3) - \beta_{m-1}) \quad (18)$$

and at angle $\beta_m$, $$\sin(\theta_1 - \sin^{-1}(n_1/n_2 \sin(\theta_1+\beta_m))) = n_1/n_2 \sin(\tan^{-1}(d^{m'}_2/d_3) - \beta_m) \quad (19)$$

$$\sin(\Phi_1 - \sin^{-1}(n_1/n_2 \sin(\Phi_1+\beta_m))) = n_1/n_2 \sin(\tan^{-1}(d^{m'}_1/d_3) - \beta_m) \quad (20)$$

In one embodiment, equations (9) through (20) can be resolved for $\theta_1$, $\Phi_1$, and $n_2$ by using the equation (21) below:

$$\sqrt{\Sigma(RHS-LHS)^2} = 0 \quad (21)$$

where $\Sigma$ is the summation over all 2m equations, wherein RHS refers to the factors on the right hand side of the equations (9) through (20) and wherein LHS refers to those factors on the left hand side of the equations (9) through (20). In one embodiment, equation (21) can be solved numerically if desired. This is accomplished by using a numerical minimization scheme.

In another embodiment, by solving the 2m equations, it is possible to obtain a greater degree of accuracy in determining values for $\theta_1$, $\Phi_1$ and $n_2$ and thus for the apex angle and the skew angle as well. In one embodiment, by taking measurements at "m" different angles of $\beta$ up to an angle of $\beta_m$, it is possible to obtain a large population of values for $\theta_1$, $\Phi_1$ and $n_2$. The large population of values may be used to determine statistical bounds for $\theta_1$, $\Phi_1$ and $n_2$ and thus for the apex angle and the skew angle as well. By obtaining a large population of values, effective confidence intervals may be computed for the prism sheet as well as for manufacturing processes that are used to manufacture the prism sheets. In one embodiment, it is desirable to conduct "m" measurements that permit obtaining values for $\theta_1$, $\Phi_1$ and $n_2$ with at least 95% confidence.

The obtaining of multiple values for $\theta_1$, $\Phi_1$ and $n_2$ and averaging these values is useful because it can help overcome two sources of potential error in the method of measurement, which are as follows: a) the incident light source has a finite width which leads to a "spread" of the projected images on the ruled scale and b) the resolution with the parameters $d_1$, $d_2$, $d_3$ and $\beta$ can be measured. It is also to be noted that higher angles of $\beta$ (empirically) give rise to additional measurement error because it's harder to read the values off the ruled scale. Thus, there is a limit to the number of rotational angles $\beta$ through which the prism sheet can be rotated in order to make measurements.

Notwithstanding its limitations, the above-described method and apparatus are advantageous in that it they can be used to examine prism sheets without destroying the prism sheet. This is a cost effective, sensitive method for simultaneously measuring the apex angle, the skew angle and the refractive index of micro-structured prisms and sheets. The sheets for which the aforementioned geometrical values can be obtained can be made from a single material or multiple materials. The microstructures, such as, for example, the prisms can be molded embossed, extruded or cast on one or more substrate layers.

The following examples, which are meant to be exemplary, not limiting, illustrate the method and the apparatus for determining the apex angle, the skew angle and the refractive index described herein.

EXAMPLES

Example 1

This example demonstrates using the disclosed method to calculate the refractive index, apex angle and alignment angle of a prism sheet. Although the coupled non-linear equations described above (e.g., equations (1) and (3) or (2) and (4)) can be solved by using only two rotation angles $\beta$, to increase the confidence interval of the calculated values, measurements can be taken at more rotation angles and averaged. Several factors contribute to measurement error, primarily the ability to resolve the location of the spots on the ruled scale $d_1$ and $d_2$, and the ability to resolve the rotation angle of the sample holder $\beta$. In the case of $d_1$ and $d_2$, the width of the incident light beam affects the spot size projected onto the ruled scale: a narrower beam leads to a better defined spot. This example demonstrates how the measurement accuracy can be improved by taking measurements of a given sample at more than two angles.

The light source 2 is a 633 nanometer helium neon (HeNe) laser that operates at a power of 1 milliwatt (mW). The sample film is a brightness enhancing film (BEF2) film manufactured by 3M. The ruled scale is placed 55.4 centimeters from the sample holder. The projected light spots are measured at 9 rotation angles ranging from −20 to +20 degrees in 5 degree increments. The experimental data is shown in the Table 1 below:

TABLE 1

| $\beta$ degrees | $d_1$ centimeter | $d_2$ centimeter |
|---|---|---|
| 20 | −34.8 | 40.2 |
| 15 | −33.3 | 37.2 |
| 10 | −32.3 | 35.4 |
| 5 | −31.9 | 33.8 |
| 0 | −33 | 32.5 |
| −5 | −34.3 | 32 |
| −10 | −35.7 | 31.8 |
| −15 | −38.6 | 32.7 |
| −20 | −41.5 | 34 |

Figure 7:
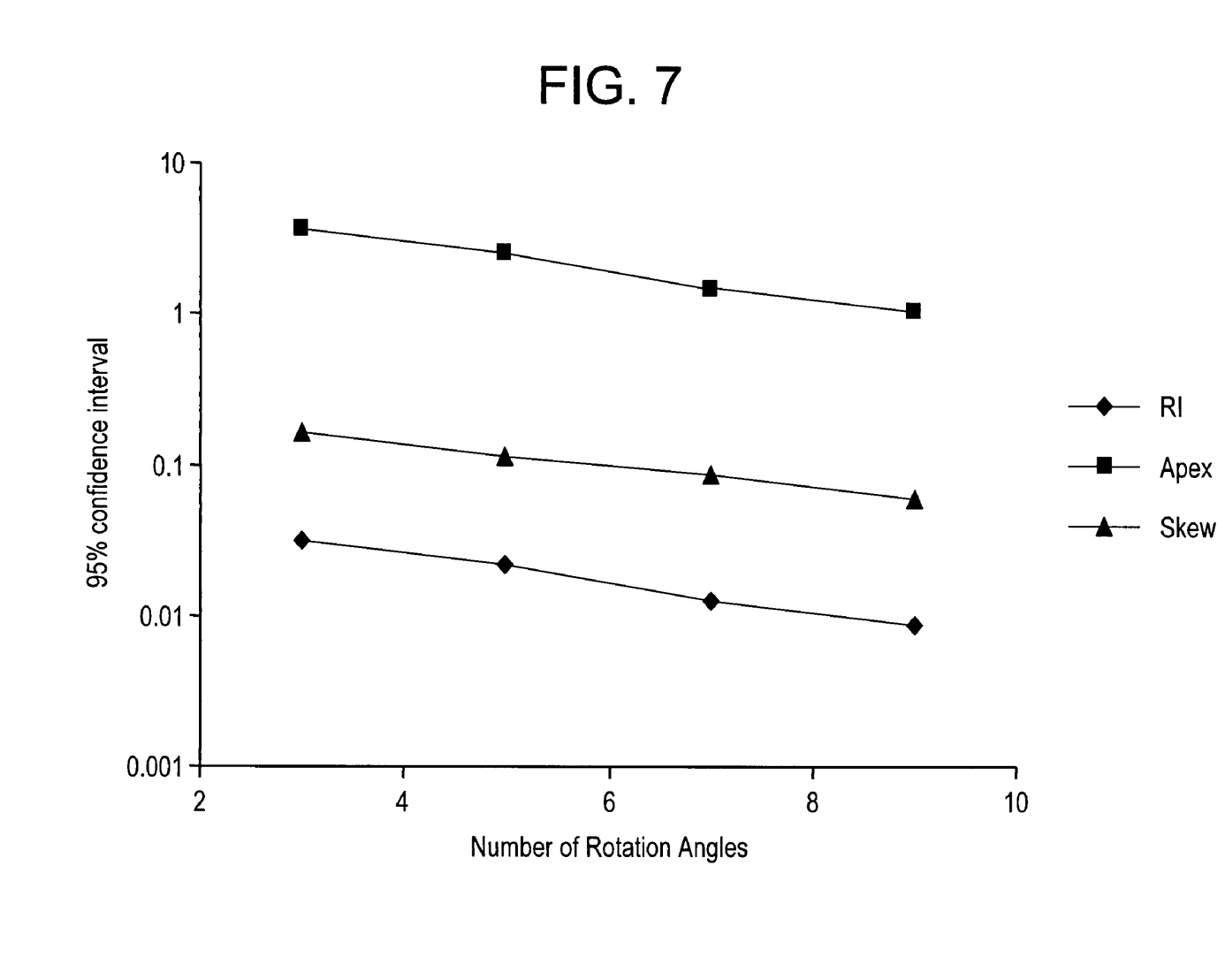
FIG. 7 is a graphical representation showing the decrease in 95% confidence intervals for the calculated refractive index, apex angle and skew angle values by increasing the number of rotation angles β.

Using the measured data, Equations (1),(2),(3) and (4) are solved over all pairwise combinations of 9 rotation angles (9×(9−1)/2=36 pairs) and the calculated values of refractive index, apex angle and skew angle are averaged. The calculated refractive index is 1.597+/−0.009 with 95% confidence. The calculated apex angle is 90.4+/−1.01 degrees with 95% confidence. The calculated skew angle is 0.165 degrees +/−0.06 with 95% confidence. Increasing the number of rotation angles $\beta$ decreases the 95% confidence intervals for the calculated refractive index, and skew angle values, as shown in the FIG. 7.

Example 2

This example demonstrates an alternative method of solving the coupled equations. Using the same experimental data table shown above, the equations are solved for all 9 rotation angles simultaneously, instead of solving for all pairwise rotation angles and averaging the calculated values. This is accomplished by using a numerical minimization scheme. Using this simplified method, the calculated refractive index is 1.595, the calculated apex angle is 90.4, and the calculated skew angle is 0.265. The refractive index and apex values are well within the confidence interval of the full calculations performed in Example 1. The skew angle is just beyond the confidence interval calculated in Example 1. Taking additional measurements or refining the minimization scheme itself should reduce the error in the values derived using this simplified method.

Example 3

This example demonstrates using the disclosed method to measure the refractive index of a prism sheet of known composition. Using the disclosed method, the refractive index of an embossed polycarbonate prism sheet was calculated to be 1.589. In comparison, a polycarbonate film measured in a Metricon 2010 prism coupler using an incident HeNe laser beam with the same wavelength (632.8 nm) had a measured refractive index of 1.588+/−0.0008 with 95% confidence.

Example 4

This example demonstrates how a prism sheet deviating from an ideal geometry affects the performance of the prism film when assembled inside a backlight module. The luminance of three brightness enhancing display sheets was tested as follows. The films are internal GE samples made by micro-replicating arrays of randomized prisms using a UV coating process with a proprietary high refractive index coating on a polycarbonate base film. The randomized prisms were manufactured from a mixture of acrylate monomers that were cast against a mold and UV-cured to replicate the mold. Each of the three sheets was made using a different mold. A bottom diffuser is placed in a backlight with an inverter. The bottom diffuser is a D120® commercially available from Tsujiden Co. Ltd, while the backlight is a LG Philips LP121X1® backlight having a single cold cathode fluorescent light (CCFL) as the source of illumination. The inverter is a LS390® inverter commercially available from Taiyo Yuden. A light management film in the vertical configuration is placed over the bottom diffuser. A light management film in the horizontal configuration is placed over the vertical light management film. In order to make the luminance measurement on a particular light management film, the light management film was cut into 2 portions. One portion was used in the vertical configuration and the other portion was used in the horizontal configuration.

Several thermocouples monitor the temperature of the backlight. After each set of samples is installed in the activated backlight, the system is allowed to equilibrate until the backlight temperature remains steady to within 0.1 degrees over the course of 5 minutes. After the system is equilibrated, a SS220® Display Analysis System commercially available from Microvision is used to measure 13 point luminance uniformity and the view angle at the center point. Performance is measured in "relative luminance" units compared to a brightness enhancing film (BEF2) film manufactured by 3M.

The disclosed method was used to calculate the refractive index, apex angle and skew angle of three internal GE samples. In all samples, the target apex angle is 90 degrees and the target skew angle is zero degrees. The results are shown in Table 2 below:

TABLE 2

|  | Sample #1 | Sample #2 | Sample #3 |
|---|---|---|---|
| Apex angle | 92.7 | 91 | 90.6 |
| Skew angle | −1.54 | −1.15 | −0.21 |
| Refractive index | 1.62 | 1.61 | 1.61 |
| Relative luminance | 99 | 103.1 | 106.8 |

From the Table 2 it may be seen that there is an increase in the relative luminance as the apex angle becomes closer to 90 degrees. This supports the premise that any deviations from an apex angle of 90 degrees and a skew angle of 0 degrees leads to reduced performance in the assembled product.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method comprising:
    illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface; and wherein a third surface of the microstructured prism contacts a surface of a sheet substrate of the prism sheet; and further wherein the third surface is inclined at an angle of 90 degrees to the incident light beam;
    measuring a first distance "$d_1$" between a first image and a perpendicular to the surface of the substrate sheet on a measuring device that is disposed on an opposite side of the prism sheet from a light source used for the illuminating; wherein the perpendicular to the surface of the substrate sheet is taken at a point where the bisector of the apex angle of the prism meets the surface of the substrate sheet in contact with the third surface of the prism; and wherein the first image is obtained by refraction of the light beam from the first surface;
    measuring a second distance "$d_2$" between a second image and a perpendicular to the surface of the substrate sheet on the measuring device; wherein the second image is obtained by refraction of the light beam from the second surface;
    substituting values for $d_1$ and $d_2$ in the equation (1) and (2) below:

$$\sin(\theta_1 - \sin^{-1}(n_1/n_2 \sin(\theta_1))) = n_1/n_2 \sin(\tan^{-1}(d_2/d_3)) \quad (1)$$

$$\sin(\Phi_1 - \sin^{-1}(n_1/n_2 \sin(\Phi_1))) = n_1/n_2 \sin(\tan^{-1}(d_1/d_3)) \quad (2)$$

wherein "$d_3$" is the distance between the prism sheet and the measuring device, $n_1$ is the refractive index of the media in which the measurement is made and $n_2$ is the refractive index of the prism sheet; and
determining at least one value for either $\theta_1$, $\Phi_1$ or $n_2$.

2. The method of claim 1, further comprising rotating the prism sheet or the light source through an angle β, wherein the angle β is the difference in angle between the position occupied by the prism sheet when it is perpendicular to the incident light beam and the position occupied by the prism sheet after rotation.

3. The method of claim 2, further comprising measuring a third distance "$d'_1$" between a third image and a perpendicular to the surface of the substrate sheet on a measuring device; wherein the third image is obtained by refraction of the light beam from the first surface; and measuring a fourth distance "$d'_2$" between a fourth image and a perpendicular to the surface of the substrate sheet on the measuring device; wherein the fourth image is obtained by refraction of the light beam from the second surface; and simultaneously determining at least one value for either $\theta_1$, $\Phi_1$ or $n_2$ for the prism sheet from the equations (1), (2), (3) and (4)

$$\sin(\theta_1 - \sin^{-1}(n_1/n_2 \sin(\theta_1 + \beta))) = n_1/n_2 \sin(\tan^{-1}(d'_2/d_3) - \beta) \quad (3)$$

$$\sin(\Phi_1 - \sin^{-1}(n_1/n_2 \sin(\Phi_1 + \beta))) = n_1/n_2 \sin(\tan^{-1}(d'_1/d_3) - \beta) \quad (4)'.$$

4. The method of claim 1, wherein the incident light beam is a laser light.

5. The method of claim 1, wherein the incident light beam illuminates more than one prism.

6. The method of claim 1, wherein the measuring device is a ruled scale.

7. The method of claim 1, further comprising determining the prism apex angle by using the equation:

Prism Apex angle=180−($\theta_1$−$\Phi_1$).

8. The method of claim 3, further comprising determining the prism apex angle by using the equation:

Prism Apex angle=180−($\theta_1$−$\Phi_1$).

9. The method of claim 1, further comprising determining the skew angle by using the equation:

Skew angle=($\theta_1$+$\Phi_1$)/2.

10. The method of claim 3, further comprising determining the skew angle by using the equation:

Skew angle=($\theta_1$+$\Phi_1$)/2.

11. An apparatus that uses the method of claim 1.
12. An apparatus that uses the method of claim 3.
13. A method comprising:
    illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface; and wherein a third surface of the microstructured prism contacts a surface of a sheet substrate of the prism sheet;

measuring a first distance "$d_1$" between a first image and a perpendicular to the surface of the substrate sheet on a measuring device that is disposed on an opposite side of the prism sheet from a light source used for the illuminating; wherein the perpendicular to the surface of the substrate sheet is taken at a point where the bisector of the apex angle of the prism meets the surface of the substrate sheet in contact with the third surface of the prism; and wherein the first image is obtained by refraction of the light beam from the first surface;

measuring a second distance "$d_2$" between a second image and a perpendicular to the surface of the substrate sheet on the measuring device; wherein the second image is obtained by refraction of the light beam from the second surface;

rotating the prism sheet or the light source through an angle β; wherein the angle β is the difference in angle between the position occupied by the prism sheet when it is perpendicular to the incident light beam and the position occupied by the prism sheet after rotation;

measuring a third distance "$d'_1$" between a third image and a perpendicular to the surface of the substrate sheet on a measuring device; wherein the third image is obtained by refraction of the light beam from the first surface;

measuring a fourth distance "$d'_2$" between a fourth image and a perpendicular to the surface of the substrate sheet on the measuring device; wherein the fourth image is obtained by refraction of the light beam from the second surface; and simultaneously determining $\theta_1$, $\Phi_1$ and $n_2$ of the microstructured prism from the equations (1), (2), (3) and (4)

$$\sin(\theta_1 - \sin^{-1}(n_1/n_2 \sin(\theta_1))) = n_1/n_2 \sin(\tan^{-1}(d_2/d_3)) \quad (1)$$

$$\sin(\Phi_1 - \sin^{-1}(n_1/n_2 \sin(\Phi_1))) = n_1/n_2 \sin(\tan^{-1}(d_1/d_3)) \quad (2)$$

$$\sin(\theta_1 - \sin^{-1}(n_1/n_2 \sin(\theta_1+\beta))) = n_1/n_2 \sin(\tan^{-1}(d'_2/d_3) - \beta) \quad (3)$$

$$\sin(\Phi_1 - \sin^{-1}(n_1/n_2 \sin(\Phi_1+\beta))) = n_1 i/n_2 \sin(\tan^{-1}(d'_1/d_3) - \beta) \quad (4)$$

wherein "$d_3$" is the distance between the prism sheet and the measuring device, $n_1$ is the refractive index of the media in which the measurement is made and $n_2$ is the refractive index of the prism sheet.

14. The method of claim 13, wherein the incident light beam is a laser light.

15. The method of claim 13, wherein the prism sheet is disposed in an angular micrometer.

16. The method of claim 13, wherein the measuring device is a ruled scale.

17. The method of claim 13, further comprising determining the prism apex angle by using the equation:

Prism Apex angle=180−($\theta_1$−$\Phi_1$).

18. The method of claim 13, further comprising determining the skew angle by using the equation:

Skew angle=($\theta_1$+$\Phi_1$)/2.

19. An apparatus that uses the method of claim 13.

20. A method comprising:

illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface; wherein a third surface of the microstructured prism contacts a surface of a sheet substrate of the prism sheet; and further wherein the third surfaced is inclined at an angle of (90+β) degrees to the incident light beam;

measuring a first distance "$d_1$" between a first image and a perpendicular to the surface of the substrate sheet on a measuring device that is disposed on an opposite side of the prism sheet from a light source used for the illuminating; wherein the perpendicular to the surface of the substrate sheet is taken at a point where the bisector of the apex angle of the prism meets the surface of the substrate sheet in contact with the third surface of the prism; and wherein the first image is obtained by refraction of the light beam from the first surface;

measuring a second distance "$d_2$" between a second image and a perpendicular to the surface of the substrate sheet on the measuring device; wherein the second image is obtained by refraction of the light beam from the second surface;

substituting values for $d_1$ and $d_2$ in the equation (3) and (4) below:

$$\sin(\theta_1 - \sin^{-1}(n_1/n_2 \sin(\theta_1+\beta))) = n_1/n_2 \sin(\tan^{-1}(d'_2/d_3) - \beta) \quad (3)$$

$$\sin(\Phi_1 - \sin^{-1}(n_1/n_2 \sin(\Phi_1+\beta))) = n_1/n_2 \sin(\tan^{-1}(d'_1/d_3) - \beta) \quad (4)$$

wherein "$d_3$" is the distance between the prism sheet and the measuring device, $n_1$ is the refractive index of the media in which the measurement is made and $n_2$ is the refractive index of the prism sheet; and determining at least one value for the apex angle, the skew angle or the refractive index from the equations (3) and (4).

21. An apparatus that uses the method of claim 20.

22. A method comprising:

illuminating a first surface and a second surface of a microstructured prism on a prism sheet with an incident light beam; wherein the microstructured prisms are disposed upon a substrate sheet; and wherein a back surface of the sheet substrate is perpendicular to the incident light beam;

measuring a first distance "$d_1$" between a first image and a perpendicular to the back surface of the substrate sheet on a measuring device that is disposed on an opposite side of the prism sheet from a light source used for the illuminating;

measuring a second distance "$d_2$" between a second image and the perpendicular to the back surface of the substrate sheet on the measuring device;

substituting values for $d_1$ and $d_2$ in the equation (1) and (2) below:

$$\sin(\theta_1 - \sin^{-1}(n_1/n_2 \sin(\theta_1))) = n_1/n_2 \sin(\tan^{-1}(d_2/d_3)) \quad (1)$$

$$\sin(\Phi_1 - \sin^{-1}(n_1/n_2 \sin(\Phi_1))) = n_1/n_2 \sin(\tan^{-1}(d_1/d_3)) \quad (2)$$

wherein "$d_3$" is the distance between the prism sheet and the measuring device, $n_1$ is the refractive index of the media in which the measurement is made and $n_2$ is the refractive index of the prism sheet; $\theta_1$ is the angle between a normal to the first surface and the incident light beam and $\Phi_1$ is the angle between a normal to the second surface and the incident light beam; and determining at least one value for either $\theta_1$, $\Phi_1$ or $n_2$.

23. The method of claim 22, further comprising determining the prism apex angle by using the equation:

Prism Apex angle=$180-(\theta_1-\Phi_1)$.

24. The method of claim 22, further comprising determining the skew angle by using the equation:

Skew angle=$(\theta_1+\Phi_1)/2$.

25. An apparatus that uses the method of claim 22.

26. A method comprising:

illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface; wherein a back surface of the prism sheet is inclined at an angle of $(90+\beta)$ degrees to the incident light beam;

measuring a first distance "$d_1$" between a first image and a perpendicular to the surface of the substrate sheet on a measuring device that is disposed on an opposite side of the prism sheet from a light source used for the illuminating;

measuring a second distance "$d_2$" between a second image and the perpendicular to the surface of the substrate sheet on the measuring device;

substituting values for $d_1$ and $d_2$ in the equation (3) and (4) below:

$$\sin(\theta_1-\sin^{-1}(n_1/n_2 \sin(\theta_1+\beta)))=n_1/n_2 \sin(\tan^{-1}(d'_2/d_3)-\beta) \quad (3)$$

$$\sin(\Phi_1-\sin^{-1}(n_1/n_2 \sin(\Phi_1+\beta)))=n_1/n_2 \sin(\tan^{-1}(d'_1/d_3)-\beta) \quad (4)$$

wherein "$d_3$" is the distance between the prism sheet and the measuring device, $n_1$ is the refractive index of the media in which the measurement is made and $n_2$ is the refractive index of the prism sheet; and determining at least one value for the apex angle, the skew angle or the refractive index from the equations (3) and (4).

27. The method of claim 26, further comprising determining the prism apex angle by using the equation:

Prism Apex angle=$180-(\theta_1-\Phi_1)$.

28. The method of claim 26, further comprising determining the skew angle by using the equation:

Skew angle=$(\theta_1+\Phi_1)/2$.

29. An apparatus that uses the method of claim 26.

30. A method comprising:

illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface; and wherein a back surface of the prism sheet is perpendicular to the incident light beam;

measuring a first distance "$d_1$" between a first image and a perpendicular to the surface of the substrate sheet on a measuring device that is disposed on an opposite side of the prism sheet from a light source used for the illuminating;

measuring a second distance "$d_2$" between a second image and a perpendicular to the surface of the substrate sheet on the measuring device;

rotating the prism sheet or the light source through an angle $\beta$; wherein the angle $\beta$ is the difference in angle between the position occupied by the prism sheet when its back surface is perpendicular to the incident light beam and the position occupied by the prism sheet after rotation;

measuring a third distance "$d'_1$" between a third image and a perpendicular to the surface of the substrate sheet on a measuring device;

measuring a fourth distance "$d'_2$" between a fourth image and a perpendicular to the surface of the substrate sheet on the measuring device; and simultaneously determining $\theta_1$, $\Phi_1$ and $n_2$ of the microstructured prism from the equations (1), (2), (3) and (4)

$$\sin(\theta_1-\sin^{-1}(n_1/n_2 \sin(\theta_1)))=n_1/n_2 \sin(\tan^{-1}(d_2/d_3)) \quad (1)$$

$$\sin(\Phi_1-\sin^{-1}(n_1/n_2 \sin(\Phi_1)))=n_1/n_2 \sin(\tan^{-1}(d_1/d_3)) \quad (2)$$

$$\sin(\theta_1-\sin^{-1}(n_1/n_2 \sin(\theta_1+\beta)))=n_1/n_2 \sin(\tan^{-1}(d'_2/d_3)-\beta) \quad (3)$$

$$\sin(\Phi_1-\sin^{-1}(n_1/n_2 \sin(\Phi_1+\beta)))=n_1/n_2 \sin(\tan^{-1}(d'_1/d_3)-\beta) \quad (4)$$

wherein "$d_3$" is the distance between the prism sheet and the measuring device, $n_1$ is the refractive index of the media in which the measurement is made and $n_2$ is the refractive index of the prism sheet.

31. The method of claim 30, further comprising determining the prism apex angle by using the equation:

Prism Apex angle=$180-(\theta_1-\Phi_1)$.

32. The method of claim 30, further comprising determining the skew angle by using the equation:

Skew angle=$(\theta_1+\Phi_1)/2$.

33. An apparatus that uses the method of claim 30.

34. A method comprising:

illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface;

rotating the prism sheet or the light source through a series of angles $\beta_1$, $\beta_2$, $\beta_3$, $\beta_4$, ..., $\beta_{m-1}$, $\beta_m$, wherein each of the angles $\beta_1$, $\beta_2$, $\beta_3$, $\beta_4$, ..., $\beta_{m-1}$, $\beta_m$, is the difference in angle between a position occupied by the prism sheet and the position occupied by the prism sheet prior to rotation; where m represents the number of rotational angles that the prism sheet $\beta$ is rotated through;

measuring distances $d'_1$ and $d'_2$ at a rotational angle $\beta_1$, $d''_1$ and $d''_2$ at a rotational angle $\beta_2$, $d'''_1$ and $d'''_2$ at a rotational angle $\beta_3$, $d''''_1$ and $d''''_2$ at a rotational angle $\beta_4$, $d^{(m-1)'}_1$ and $d^{(m-1)'}_2$ at a rotational angle $\beta_{m-1}$ and $d^{m'}_1$ $d^{m'}_2$ at a rotational angle $\beta_m$; wherein the distances are measured between an image and a perpendicular to a back surface of the prism sheet on a measuring device that is disposed on an opposite side of the prism sheet from a light source used for the illuminating;

substituting the distances in the equations (9) through (20) below:

at angle $\beta_1$, $$\sin(\theta_1 - \sin^{-1}(n_1/n_2 \sin(\theta_1+\beta_1))) = n_1/n_2 \sin(\tan^{-1}(d'_2/d_3) - \beta_1) \quad (9)$$

$$\sin(\Phi_1 - \sin^{-1}(n_1/n_2 \sin(\Phi_1+\beta_1))) = n_1/n_2 \sin(\tan^{-1}(d'_1/d_3) - \beta_1) \quad (10)$$

at angle $\beta_2$, $$\sin(\theta_1 - \sin^{-1}(n_1/n_2 \sin(\theta_1+\beta_2))) = n_1/n_2 \sin(\tan^{-1}(d''_2/d_3) - \beta_2) \quad (11)$$

$$\sin(\Phi_1 - \sin^{-1}(n_1/n_2 \sin((\Phi_1+\beta_2))) = n_1/n_2 \sin(\tan^{-1}(d''_1/d_3) - \beta_2) \quad (12)$$

at angle $\beta_3$, $$\sin(\theta_1 - \sin^{-1}(n_1/n_2 \sin(\theta_1+\beta_3))) = n_1/n_2 \sin(\tan^{-1}(d'''_2/d_3) - \beta_3) \quad (13)$$

$$\sin(\Phi_1 - \sin^{-1}(n_1/n_2 \sin(\Phi_1+\beta_3))) = n_1/n_2 \sin(\tan^{-1}(d'''_1/d_3) - \beta_3) \quad (14)$$

at angle $\beta_4$, $$\sin(\theta_1 - \sin^{-1}(n_1/n_2 \sin(\theta_1+\beta_4))) = n_1/n_2 \sin(\tan^{-1}(d''''_2/d_3) - \beta_4) \quad (15)$$

$$\sin(\Phi_1 - \sin^{-1}(n_1/n_2 \sin(\Phi_1+\beta_4))) = n_1/n_2 \sin(\tan^{-1}(d''''_1/d_3) - \beta_4) \quad (16)$$

at angle $\beta_{m-1}$, $$\sin(\theta_1 - \sin^{-1}(n_1/n_2 \sin(\theta_1+\beta_{m-1}))) = n_1/n_2 \sin(\tan^{-1}(d^{(m-1)'}_2/d_3) - \beta_{m-1}) \quad (17)$$

$$\sin(\Phi_1 - \sin^{-1}(n_1/n_2 \sin(\Phi_1+\beta_{m-1}))) = n_1/n_2 \sin(\tan^{-1}(d^{(m-1)'}_1/d_3) - \beta_{m-1}) \quad (18)$$

and at angle $\beta_m$, $$\sin(\theta_1 - \sin^{-1}(n_1/n_2 \sin(\theta_1+\beta_m))) = n_1/n_2 \sin(\tan^{-1}(d^{m'}_2/d_3) - \beta_m) \quad (19)$$

$$\sin(\Phi_1 - \sin^{-1}(n_1/n_2 \sin(\Phi_1+\beta_m))) = n_1/n_2 \sin(\tan^{-1}(d^{m'}_1/d_3) - \beta_m) \quad (20)$$

wherein "$d_3$" is the distance between the prism sheet and the measuring device, $n_1$ is the refractive index of the media in which the measurement is made and $n_2$ is the refractive index of the prism sheet;

determining "m-1" values for $\theta_1$ and $\Phi_1$ respectively and "2(m-1)" values of $n_2$; and determining an average value for $\theta_1$, $\Phi_1$ and $n_2$ from the "m-1" values of $\theta_1$ and $\Phi_1$ respectively and the "2(m-1)" values of $n_2$.

35. The method of claim 34, wherein the equations (9) through (20) can be resolved for $\theta_1$, $\Phi_1$, and $n_2$ by using the equation (21) below:

$$\sqrt{\Sigma(RHS-LHS)^2} = 0 \quad (21)$$

where $\Sigma$ is the summation over all 2m equations, wherein RHS refers to the factors on the right hand side of the equations (9) through (20) and wherein LHS refers to those factors on the left hand side of the equations (9) through (20).

36. The method of claim 35, wherein the equation (21) is solved numerically.

37. The method of claim 36, wherein the equation (21) is solved via numerical minimization.

38. The method of claim 34, further comprising determining the prism apex angle by using the equation:

Prism Apex angle = $180 - (\theta_1 - \Phi_1)$.

39. The method of claim 34, further comprising determining the skew angle by using the equation:

Skew angle = $(\theta_1 + \Phi_1)/2$.

40. The method of claim 35, further comprising determining the prism apex angle by using the equation:

Prism Apex angle = $180 - (\theta_1 - \Phi_1)$.

41. The method of claim 35, further comprising determining the skew angle by using the equation:

Skew angle = $(\theta_1 + \Phi_1)/2$.

42. An apparatus that uses the method of claim 35.

43. A method comprising:

illuminating a first surface and a second surface of a microstructured prism on a prism sheet with an incident light beam; wherein the first surface is illuminated by the incident light beam at an angle $\theta_1$ with respect to a normal drawn to the first surface and wherein the second surface is illuminated by the incident light beam at an angle $\Phi_1$ with respect to a normal drawn to the second surface;

rotating the prism sheet or the light source through m angles of $\beta$; where m is a positive integer;

measuring distances $d^{m'}_1$ and $d^{m'}_2$ at a rotational angle $\beta_m$; where $\beta_m$ represents the $m^{th}$ angle of $\beta$; wherein the distances $d^{m'}_1$ and $d^{m'}_2$ are measured between an image and a perpendicular to a back surface of the prism sheet on a measuring device that is disposed on an opposite side of the prism sheet from a light source used for the illuminating; and substituting distances $d^{m'}_1$ and $d^{m'}_2$ in the equations (19) and (20)

$$\sin(\theta_1 - \sin^{-1}(n_1/n_2 \sin(\theta_1+\beta_m))) = n_1/n_2 \sin(\tan^{-1}(d^{m'}_2/d_3) - \beta_m) \quad (19)$$

$$\sin(\Phi_1 - \sin^{-1}(n_1/n_2 \sin(\Phi_1+\beta_m))) = n_1/n_2 \sin(\tan^{-1}(d^{m'}_1/d_3) - \beta_m) \quad (20)$$

wherein "$d_3$" is the distance between the prism sheet and the measuring device, $n_1$ is the refractive index of the media in which the measurement is made and $n_2$ is the refractive index of the prism sheet;

determining "m-1" values for $\theta_1$ and $\Phi_1$ respectively and "2(m-1)" values of $n_2$; and determining an average value for $\theta_1$, $\Phi_1$ and $n_2$ from the "m-1" values of $\theta_1$ and $\Phi_1$ respectively and the "2(m-1)" values of $n_2$.

44. The method of claim 43, wherein m is an integer having values of 1 to 100.

45. The method of claim 44, wherein m is selected to yield values of $\theta_1$, $\phi_1$ and $n_2$ that have at least 95% confidence.

46. The method of claim 42, wherein all 2m equations generated by substituting m distances of $d^{m'}_1$ and $d^{m'}_2$ in equations (19) and (20) can be resolved for $\theta_1$, $\Phi_1$, and $n_2$ by using the equation (21) below:

$$\sqrt{\Sigma(RHS-LHS)^2} = 0 \quad (21)$$

where $\Sigma$ is the summation over all 2m equations, wherein RHS refers to the factors on the right hand side of the equations (19) and (20) and wherein LHS refers to those factors on the left hand side of the equations (19) and (20).

47. The method of claim 46, wherein the equation (21) is solved numerically.

48. The method of claim 47, wherein the equation (21) is solved via numerical minimization.

49. The method of claim 43, further comprising determining the prism apex angle by using the equation:

Prism Apex angle=$180-(\theta_1-\Phi_1)$.

50. The method of claim 43, further comprising determining the skew angle by using the equation:

Skew angle=$(\theta_1+\Phi_1)/2$.

51. The method of claim 44, further comprising determining the prism apex angle by using the equation:

Prism Apex angle=$180-(\theta_1-\Phi_1)$.

52. The method of claim 44, further comprising determining the skew angle by using the equation:

Skew angle=$(\theta_1+\Phi_1)/2$.

* * * * *